United States Patent [19]

Oldenhove de Guertechin

[11] Patent Number: 5,639,450
[45] Date of Patent: Jun. 17, 1997

[54] CLEANSING AND CONDITIONING COSMETIC COMPOSITION

[75] Inventor: Louis Oldenhove de Guertechin, Heks, Belgium

[73] Assignee: Colgate-Palmolive Company, New York, N.Y.

[21] Appl. No.: 356,806

[22] Filed: Dec. 15, 1994

[51] Int. Cl.$^6$ ................................ A61K 7/48; A61K 7/50
[52] U.S. Cl. ............................. 424/70.19; 424/70.31; 510/138
[58] Field of Search .................. 424/70.19, 70.31, 424/401; 252/DIG. 5

[56] References Cited

U.S. PATENT DOCUMENTS

| | | | |
|---|---|---|---|
| 3,228,842 | 1/1966 | Barkland et al. | 167/87 |
| 3,988,255 | 10/1976 | Seidon | 252/107 |
| 4,268,410 | 5/1981 | Allan et al. | 252/312 |
| 4,488,564 | 12/1984 | Grollier et al. | 132/7 |
| 4,707,293 | 11/1987 | Ferro | 252/174.17 |
| 4,963,535 | 10/1990 | Sebag et al. | 514/54 |
| 5,298,240 | 3/1994 | Schroder et al. | 424/70.31 |

*Primary Examiner*—Sallie M. Gardner
*Attorney, Agent, or Firm*—Martin B. Barancik

[57] ABSTRACT

An oily single phase combination cleansing, conditioning composition comprising
- a. an oil of polarity lower than component b. and having skin conditioning properties,
- b. a nonionic surfactant of HLB of about 3 to about 6, and
- c. a second nonionic surfactant of HLB of about 7 to about 15, the quantities of a, b and c selected so that there is a single phase of a, b and c with no more than 2 wt. % water and significant quantities of a is deposited on skin once water is added to the composition.

8 Claims, No Drawings

CLEANSING AND CONDITIONING COSMETIC COMPOSITION

BACKGROUND OF THE INVENTION

There are a multiplicity of cleansing products and conditioning products in the marketplace. Generally the cleansing products are aqueous based so as to remove soil from skin and/or hair surface upon rinsing. Conditioning products are intended to deposit a substance on the skin or hair and are usually present in a non aqueous oily type system. Various "2 in 1" products are now on the marketplace. These attempt to both cleanse and condition the hair or skin. Many of these are emulsions of the oily conditioning agents and the aqueous cleanser system are usually in oil in water form. Much difficulty is had in preparing a stable multiphase system, emulsion, which has a significant shelflife. The emulsions have a tendency to break apart into their separate phases. Additionally, it is extremely difficult to achieve the concomitant cleansing and conditioning of skin and hair. Although there may be an increased sensory perception by the user of the composition, the actual deposition of conditioning agent is generally below the minimum amount which brings about a real measurable effect on the skin or hair. Furthermore, they are generally not readily water rinsable and tend to leave a greasy feeling on the skin. Therefore, there exists a real need for a composition which both cleanses the skin and/or hair and concomitantly lays down a layer of conditioning agent.

This goal has been accomplished by a novel single phase oily composition bearing a minimum of three components of differing polarities and functions within the composition. The composition is applied to the skin and removes soil therefrom. When water is added to the skin bearing the composition, an emulsion is then made with the least polar component of the composition precipitating from the emulsion and depositing on the skin. This least polar material provides the conditioning effects to the skin. The two or more increasing polarity components of the composition remain in the aqueous emulsion and are removed from the skin together with skin soil. The least polar material(s) remain on the skin and condition it. Not only is general soil removed from the hair, but the composition is capable of removing "waterproof" make-ups, mascara, eye shadows and the like.

SUMMARY OF THE INVENTION

In accordance with the invention, there is an oily single phase combination cleansing, conditioning composition comprising a. an oil of polarity lower than component b and having skin conditioning properties b. a nonionic surfactant of HLB of above 3 to about 6, and c. a second nonionic surfactant of HLB of about 7 to about 15, the quantities of a, b and c selected so that there is a single phase of a, b and c with no more than 2 wt. % water and significant quantities of a is deposited on skin once water is added to the composition.

A further aspect of the invention is a method for both cleansing and conditioning the skin which comprises applying to the skin an oily single phase composition comprising a. an oil of polarity less than component b and having skin conditioning properties, b. a nonionic surfactant of HLB of about 3 to about 6, and c. a second nonionic surfacted of HLB of about 7 to about 15, the quantities of a, b and c selected so that there is a single phase of a, b and c with no more than 2 wt. % water, applying water for rinsing purposes to the composition on the skin, thereby creating an emulsion removing the emulsion from the skin including any skin soil or organic material included therein while concomitantly depositing on the skin, in skin conditioning mounts, quantities of component a.

The quantity of component a deposited on the skin concomitantly with the application of water is at least somewhat dependent on the ratio of the b and c components to each other. The more component b there is, in relationship to c, the more component a is deposited on the skin when water is applied.

DETAILED DESCRIPTION OF THE INVENTION

The concept of this invention is very broad. The nature of the components a, b and c is that they should have differing global polar character. By this character it is meant the water dispersability and/or solubility in water. The least polar material component a, has little or no water dispersability. As polarity increases, the dispersability in water increases. Component a should be the least polar and have skin conditioning effects. Component b should be a nonionic surfactant but with a relatively non polar nature, that is, having an HLB, (hydrophilicity, lipophilicity balance) as measured by the Griffin HLB scale, see Griffin W. C. J. Soc. CosmetChem. 1, 311 (1949) and J. Soc. CosmetChem. 5, 249 (1954) of about 3 to 6, preferably about 4 to 5. The third component, c, should be an even more polar nonionic surfactant and have an even higher HLB than component b. Generally this HLB is about 7 to 15, preferably 8 to 12.

The key to the action of the composition when applied to the skin is that it be a single oily phase, even with up to 2 wt. % of the system being water, preferably no more than 1 wt. %, water, most preferably in the absence of water. Therefore, the quantities of components a, b and c can vary widely as long as a single oily phase is present. Interestingly, the quantity of component a deposited on the skin is directly related to the mount of component b present. The more component b in relationship to component c then the more component a is forced from the system when water is brought into contact with the composition covering the skin.

In more detail, component a is oily and has skin conditioning effects. These oils can be linear, branched, saturated, unsaturated, and can incorporate polar functions such as the glycerides and the like. However, such materials preferably have no surfactant effects or in the alternative a maximum HLB of less than or equal to 3. A mixture of two or more oils can be employed. Examples of such component a materials include sunflower oil, rapeseed oil, coconut oil, cottonseed oil, corn oil, paraffin oils, and in general, any vegetable oil. Other oily materials, considered as skin emollients can be employed. They are generally molecules containing natural or synthetic hydrocarbon chains, having a total carbon number equal or greater than 10 and having one or more polar groups. Examples of such materials including, fatty alcohols, fatty acids, esters such as caprylates, caprates, laurates, myristates, palmitates, stearates, isosterates, oleates, ricinoleates, lanolates, rosinates, pelargonates, cocoates, tallowates, and the like diesters and triesters such as adipates, succinates, sebacates, maleates, malates, citrates, etc., mono-di- and tri-glycerides, squalene, and mixtures thereof. Mixtures of any of these oils can be used as component a. The quantity of component a, as well as the other components b and c can vary widely as long as the overall composition is a single phase and skin conditioning oil is deposited on the skin when an emulsion is made with the rinse water. Quantities of oil can be from about 50 to about 80 wt. % of the composition, preferably about 55 to 75 wt. %.

Component b is a nonionic surfactant having an HLB of above 3 to about 7, preferably 4 to 5. A mixture of two or more component b materials can be used. Examples of such materials include various sorbitan esters such as Span 80 available from ICI, as well as Cholesterol, Lanolin, Glyceryl monooleate, Sorbitan monooleate Glyceryl mono and distearate, Diethylene glycol mono stearate, Polyethylene glycol 300 monoricinoleate, Sorbitan monoisostearate, Glyceryl monolaurate, Polyethylene glycol 300 diricinoleate, Diethylene glycol monooleate, and Diethylene glycol monostearate. Quantities of this component can vary from about 4 to about 30 wt. % of the composition, preferably about 7 to 25 wt. % of the composition. This component having an intermediately polarity between component a and c serves to couple component c, most polar of these components, into the oily phase of component a.

Component c is the most polar of the three components a, b and c. It is a nonionic surfactant having an HLB of about 7 to 15, preferably about 8 to 12. A mixture of two or more component c materials can be used. Examples of such materials include non ethoxylated materials as well as certain ethoxylated materials of component b, for example, ethoxylated sorbitan ester(s) available as tween 81 from ICI. Further materials include distilled oleyl ether POE 5, polyethylene glycol 400 distearate, polyethylene glycol 300 monooleate, lauric acid POE 4, polyethylene glycol 600 diricinoleate, cethyl ether POE 5, sorbitan monostearate POE 4, castor oil POE 20, Sorbitan monooleate POE 5, polyethylene glycol 400 dilaurate, synthetic alcohol ether POE 5, polyethylene glycol 600 dioleate, sorbitan tristearate POE 20, polyethylene glycol 300 monostearate, distilled lanolin alcohols POE 10, polyethylene glycol 600 distearate, oleic acid POE 8, stearic acid POE 8, lauryl ether POE 5, lanolin acids POE 10, polyethylene glycol 400 monoricinoleate, polyethylene glycol 400 monostearate, and sorbitan trioleate POE 20, and glyceryl monolaurate POE 8. The quantity of component c is from about 10 to 55 wt. % of the composition, preferably about 15 to 50 wt. %.

It has also been discovered that the quantity of component a, oil deposited on the skin, will increase as the weight ratio of component b to component c increases. Therefore, composition of the invention can provide different levels of skin conditioning depending upon skin characteristics for example dry, mixed, greasy and the like.

The maintenance of different polarities, for each of the components is important to the carrying out of the invention. Therefore, the two surfactants, components b and c, are preferably at least 2, more preferably 3, HLB units apart. When component a might have some surfactant effect, it is also preferred to be at least 2 HLB units apart from compound b.

Other materials may be in the composition, if desired, however, the single phase must be maintained and the component c, except for the maximum 2 wt. % of a further more polar material such as water, is the most polar of the components. In this light, small quantities of a fragrance or compatible colorants, for example, may be added to the composition. These materials are generally oily in nature. The composition is applied to the face and/or hands, preferably the face, to rid the skin of organic materials, some allegedly "waterproof", such as mascara, make-up, eye shadows and other oily type materials. Water is then used to rinse off the composition containing the non rinsed organic materials. The water forms an emulsion with the composition of the invention allowing it to be readily removed. Concomitantly, at least a portion of the oily component a is no longer soluble in the composition and is deposited on the skin thereby providing to the skin a mild and silky feel.

Below are examples of the invention. These examples are intended to be descriptive but non limiting to the overall concept of the invention.

EXAMPLES—Wt.

| Component | 1 | 2 | 3 | 4 | 5 |
|---|---|---|---|---|---|
| Sunflower oil | 58.8 | 63.8 | 68.8 | 58.8 | 58.8 |
| Sorbitan ester[a] ethoxylated | 35 | 25 | 15 | 30 | 25 |
| Sorbitan ester[b] | 5 | 10 | 15 | 10 | 15 |
| Perfume | 1.2 | 1.2 | 1.2 | 1.2 | 1.2 |

[a]Tween 81, ICI
[b]Span 80, ICI

The above Examples 1–5 were all one phase. A panel of individuals assessed the composition for removal of soil and other preparation from the face such as mascara, eyeshadow, and make-up. The composition was applied easily and rubbed in readily into the skin. Water was used to rinse off the composition. The soil and other preparation, as well as the composition was readily removed. Afterwards, the skin felt mild and silky due to the film of oil that adhered to the skin from the composition.

I claim:

1. An oily single phase combination cleansing, conditioning composition comprising
   a. an oil having skin conditioning properties and having a polarity lower than a nonionic surfactant of HLB of about 3 to about 6,
   b. a nonionic surfactant of HLB of about 3 to about 6, and selected from the group consisting of sorbitan esters, Cholesterol, Lanolin, Glyceryl monooleate, Sorbitan monooleate, Glyceryl mono and distearate, Diethylene glycol mono stearate, Polyethylene glycol 300 monoricinoleate, Sorbitan monoisostearate, Glyceryl monolaurate, Polyethylene glycol 300 diricinoleate, Diethylene glycol monooleate, and Diethylene glycol monostearate and mixtures thereof, and,
   c. a second nonionic surfactant of HLB of about 7 to about 15, and selected from the group consisting of ethoxylated sorbitan esters, oleyl ether POE 5, polyethylene glycol 400 distearate, polyethylene glycol 300 monooleate, lauric acid POE 4, polyethylene glycol 600 diricinoleate, cethyl ether POE 5, sorbitan monostearate POE 4, castor oil POE 20, Sorbitan monooleate POE 5, polyethylene glycol 400 dilaurate, synthetic alcohol ether POE 5, polyethylene glycol 600 dioleate, sorbitan tristearate POE 20, polyethylene glycol 300 monostearate, distilled lanolin alcohols POE 10, polyethylene glycol 600 distearate, oleic acid POE 8, stearic acid POE 8, lauryl ether POE 5, lanolin acids POE 10, polyethylene glycol 400 monoricinoleate, polyethylene glycol 400 monostearate, sorbitan trioleate POE 20, and glyceryl monolaurate POE 8 and mixtures thereof, said composition being in the form of a liquid and
   the quantities of a, b and c selected so that there is a single phase of a, b and c with no more than 2 wt. % water wherein a is deposited on the skin upon topical application of the composition with water and there is a minimum of at least 2 HLB units between the surfactant of b and the surfactant of c.

2. The composition in accordance with claim 1 wherein a is from about 50 to 80 wt. % of the composition.

3. The composition in accordance with claim 1 wherein b is from about 4 to 30 wt. % of the composition.

4. The composition in accordance with claim 1 wherein c is from about 10 to about 55 wt. % of the composition.

5. A method for both cleansing and conditioning the skin which comprises a. applying to the skin a composition of claim 1, b. applying water for rinsing purposes to the composition on the skin, thereby crating an emulsion, c. removing the emulsion from the skin including any skin soil or organic material included therein while concomitantly depositing on the skin, skin conditioning effective quantities of a.

6. The composition in accordance with claim 1 wherein the nonionic surfactant of b is at least three HLB units apart from the nonionic surfactant of c.

7. The composition in accordance with claim 1 wherein the oil of a has a surfactant effect and has an HLB at least two units apart from the nonionic surfactatnt of b.

8. The composition in accordance with claim 1 wherein b is selected from sorbitan esters and c is selected from ethoxylated sorbitan esters.

* * * * *